(12) United States Patent
Li et al.

(10) Patent No.: US 8,455,642 B2
(45) Date of Patent: Jun. 4, 2013

(54) PHOTOSENSITIZERS FOR DSSCS

(75) Inventors: Wen-Ren Li, Taoyuan County (TW); Chao-Chin Su, Taipei (TW); Nai-Mu Hsu, Tainan (TW); Wei-Chun Chang, Keelung (TW); Huei-Siou Chen, Taipei (TW); Ting-Yu Li, Taoyuan County (TW); Chung-Yen Li, Taoyuan County (TW)

(73) Assignees: National Central University, Taoyuan County (TW); National Taipei University of Technology, Taipei (TW)

( * ) Notice: Subject to any disclaimer, the term of this patent is extended or adjusted under 35 U.S.C. 154(b) by 53 days.

(21) Appl. No.: 13/332,369

(22) Filed: Dec. 21, 2011

(65) Prior Publication Data

US 2012/0178936 A1   Jul. 12, 2012

(30) Foreign Application Priority Data

Jan. 12, 2011   (TW) .............................. 100101105 A

(51) Int. Cl.
   *C07F 15/00*   (2006.01)
   *H01L 31/042*   (2006.01)

(52) U.S. Cl.
   USPC .............................................. 546/2; 136/252

(58) Field of Classification Search
   USPC .............................................. 546/2; 136/252
   See application file for complete search history.

(56) References Cited

PUBLICATIONS

Engineering of efficient panchromatic sensitizers for nanocrystalline TiO(2)-based solar cells. Mohammad K. Nazeeruddin, Peter Péchy, Thierry Renouard, Shaik M. Zakeeruddin, Robin Humphry-Baker, Pascal Comte, Paul Liska, Le Cevey, Emiliana Costa, Valery Shklover, Leone Spiccia, Glen B. Deacon, Carlo A. Bignozzi, and Michael Gratzel. Journal of the American Chemical Society (2001), 123(8), 1613-1624.

Photoinduced Ultrafast Dye-to-Semiconductor Electron Injection from Nonthermalized and Thermalized Donor States, Gábor Benkö, Jani Kallioinen, Arkady P. Yartsev, Jouko E. I. Korppi-Tommola, and Villy Sundström. Journal of the American Chemical Society (2002), 124(3), 489-493.

High Efficiency of Dye-Sensitized Solar Cells Based on Metal-Free Indoline Dyes. Tamotsu Horiuchi, Hidetoshi Miura, Kouichi Sumioka, and Satoshi Uchida. Journal of the American Chemical Society (2004), 126(39), 12218-12219.

A ruthenium complex with superhigh light-harvesting capacity for dye-sensitized solar cells. Chia-Yuan Chen, Shi-Jhang Wu, Chun-Guey Wu, Jian-Ging Chen , Kuo-Chuan Ho. Angewandte Chemie, International Edition (2006), 45(35), 5822-5825.

Interfacial Charge Recombination Between e—TiO2 and the I-/I3—Electrolyte in Ruthenium Heteroleptic Complexes: Dye Molecular Structure-Open Circuit Voltage Relationship. Anna Reynal, Amparo Forneli, Eugenia Martinez-Ferrero, Antonio Sánchez-Díaz, Anton Vidal-Ferran, Brian C. O'Regan, and Emilio Palomares. Journal of the American Chemical Society (2008), 130(41).

Highly Efficient N-Heterocyclic Carbene/Pyridine-Based Ruthenium Sensitizers: Complexes for Dye-Sensitized Solar Cells Wei-Chun Chang, Huei-Siau Chen, Ting-Lu Li, Nai-Mu Hsu, Yogesh S. Tingare, Chung-Yen Li, Yi-Cheng Liu, Chaochin Su, and Wen-Ren Li (Angew. Chem. Int. Ed. 2010, vol. 49, p8161).

Carbene-based ruthenium photosensitizers Dalton Transactions (Dalton Trans., 2011, 40, 6765-6770) Huei-Siou Chen, Wei-Chun Chang, Chaochin Su, Ting-Yu Li, Nai-Mu Hsu, Yogesh S. Tingare, Chung-Yen Li, Jun-Han Shie and Wen-Ren Li This journal is Royal Society of Chemistry 2011.

*Primary Examiner* — Charanjit Aulakh
(74) *Attorney, Agent, or Firm* — CKC & Partners Co., Ltd.

(57) ABSTRACT

A theme of the present invention is to propose a new series of N-heterocyclic carbene-pyridine ruthenium sensitizers incorporated with at least one carbene unit and provide their synthetic methods. The structural modification on the carbene-pyridine ligand of ruthenium complexes resulted in promising photosensitizers for dye-sensitized solar cells exhibiting excellent cell performance.

8 Claims, 1 Drawing Sheet

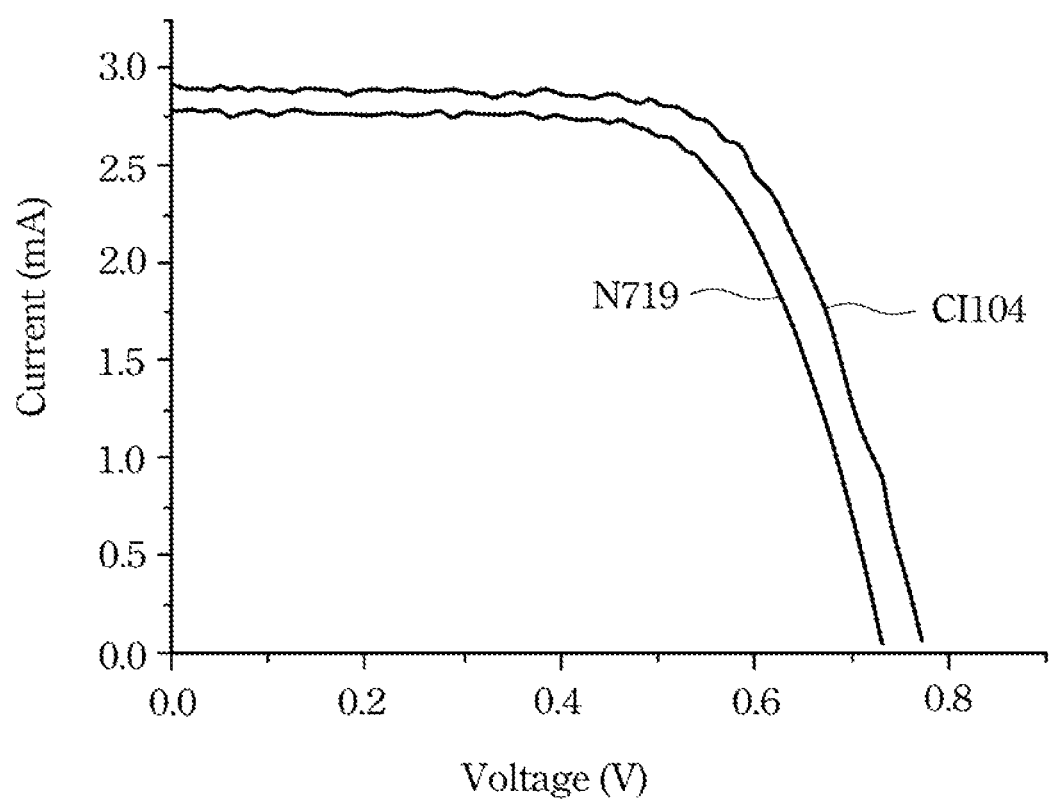

PHOTOSENSITIZERS FOR DSSCS

CROSS-REFERENCE TO RELATED APPLICATION

This application claims the priority benefit of Taiwan application serial no. 100101105, filed Jan. 12, 2011, the full disclosure of which is incorporated herein by reference.

BACKGROUND

1. Technical Field

The disclosure relates to photosensitizers. More particularly, the disclosure relates to photosensitizers for dye-sensitized solar cells.

2. Description of Related Art

Increasing energy demands and concerns over global warming have led to a greater focus on the development of renewable energy sources. With the discovery of inexpensive photovoltaic devices, dye-sensitized solar cell (DSSC) technology is emerging as a potential solution to fulfill our green energy demands. Since the initial report of DSSC in 1991, Grätzel and co-workers have investigated ruthenium polypyridyl complexes such as N3, N719, and Black dye exhibiting highly efficient light harvesting properties. During the last two decades, many ruthenium complexes were investigated for DSSC applications. However, to date, most of ruthenium sensitizers for DSSC applications that have been described in the literature are those bearing bipyridine or polypyridine ligands.

SUMMARY

Accordingly, this disclosure provides a series of novel ruthenium dyes chelated by at least one carbene ligand to improve the performance of DSSCs. The molecular structure of the photosensitizer with a ruthenium complex incorporating an N-heterocyclic carbene (NHC)-pyridine unit as an ancillary group is shown in chemical structure (I) below. Furthermore, the dipyridine ligand of the ruthenium complex in chemical structure (I) can be replaced by the second NHC-pyridine ligand to give a ruthenium complex (II) having two NHC-pyridine ligands.

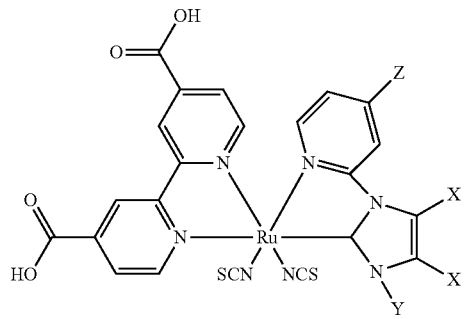
(I)

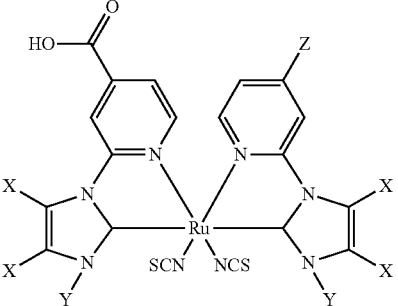
(II)

In these chemical structures (I)-(II), X is $R_a$, $N(R_a)_2$,

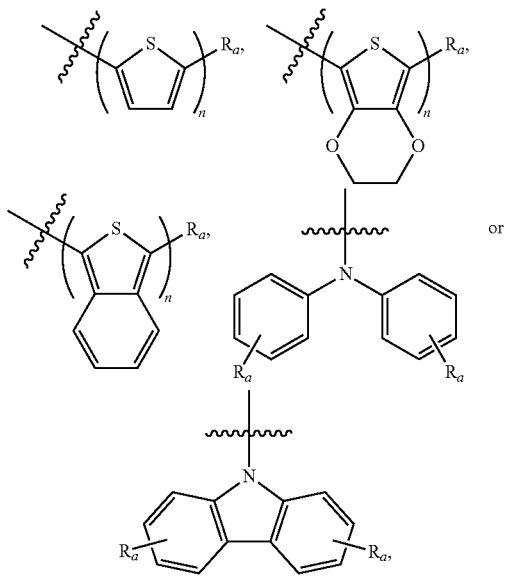

wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15) and n is 1 to 3.

Y is $R_b$,

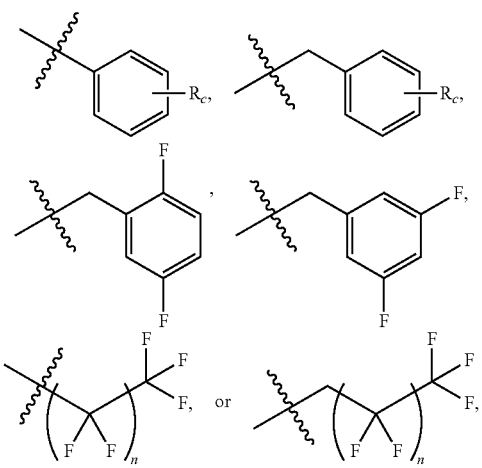

wherein $R_b$ is —H or —$C_mH_{2m+1}$ (m=1 to 15), $R_c$ is —H, —$C_mH_{2m+1}$ (m=1 to 15), —$OC_pH_{2p+1}$ (p=1 to 15) or —$SC_rH_{2r+1}$ (r=1 to 15), and n is 1 to 3.

Z is $R_a$, —$N(R_a)_2$, —COOH, —CN, —$CONH_2$, —$PO_3H_2$,

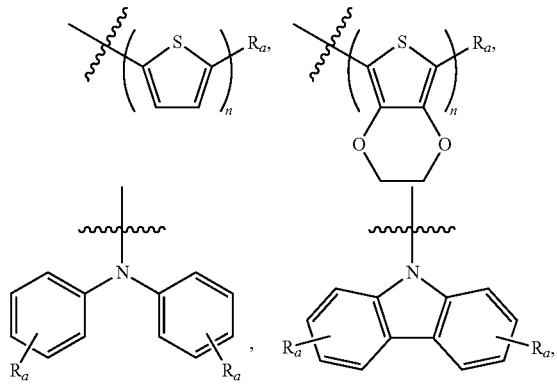

—$R_d$, or —$CONHR_d$, wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15), $R_d$ is —$C_6H_5$ or —$C_mH_{2m+1}$ (m=1 to 15), and n is 1 to 3.

Ruthenium complexes (I) and (II) above can be prepared as the followings: At first, an imidazole is reacted with 2-halopyridine to form a substituted 2-(1H-imidazol-1-yl)-pyridine. The resulting 2-(1H-imidazol-1-yl)-pyridine is alkylated with an alkylation reagent to yield an imidazole salt having the chemical structure below. Moiety Z' is the above mentioned Z substituent or a masked form of the Z moiety above. For example, Z' can has an amine functional group when the Z substituent is unmasked, or Z' can has an ester or a nitrile functional group when the substituent is masked.

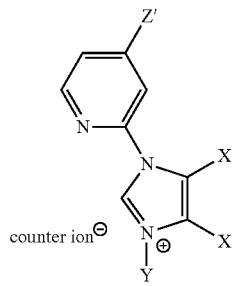

The substituted imidazole salt is then reacted with [RuCl$_2$(p-cymene)]$_2$, a ligand, and KSCN to form an protected photosensitizer. For the ruthenium complex (I), the ligand is a protected 4,4'-bis(alkoxycarbonyl)-2,2'-bipyridine. For the ruthenium complex (II), the ligand is the imidazole salt above. Finally, the masked photosensitizer was hydrolyzed under basic conditions to yield the ruthenium complex (I) or (II).

The forgoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

Many of the attendant features will be more readily appreciated as the same becomes better understood by references to the following detailed description considered in connection with the accompanying drawings.

BRIEF DESCRIPTION OF THE DRAWINGS

FIG. 1. The photocurrent density-voltage (J-V) characteristics of photovoltaic device assembled with multiple layered TiO$_2$ films and anchored with CI104 and N719 sensitizers.

DETAILED DESCRIPTION

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Chemical Structures of Ru—NHC-Pyridine Derivative Complexes

Accordingly, this disclosure provides a series of novel ruthenium dyes chelated by at least one carbene ligand to improve the performance of DSSCs. The molecular structure of the photosensitizer with a ruthenium complex incorporating an N-heterocyclic carbene (NHC)-pyridine unit as an ancillary group is shown in chemical structure (I) below. Furthermore, the dipyridine ligand of a ruthenium complex in chemical structure (I) can be replaced by the second NHC-pyridine ligand to give a ruthenium complex (II) having two NHC-pyridine ligands.

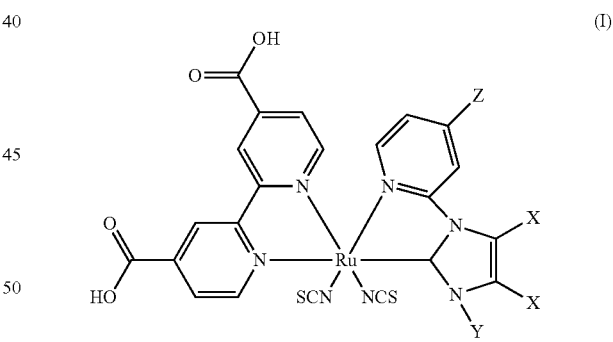

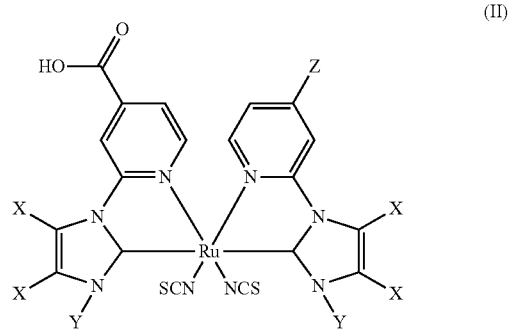

In these chemical structures (I)-(II), X is $R_a$, $N(R_a)_2$,

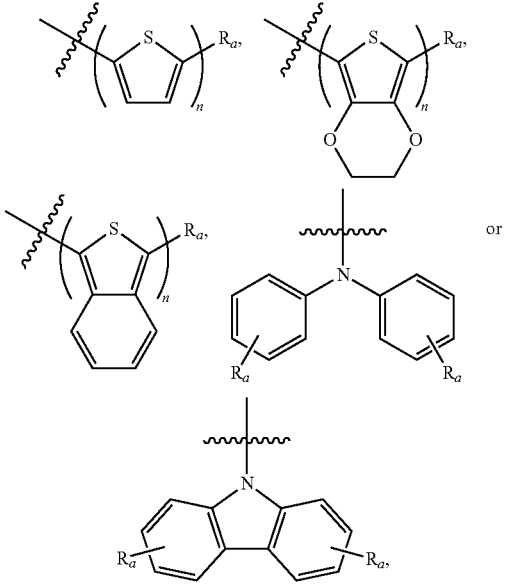

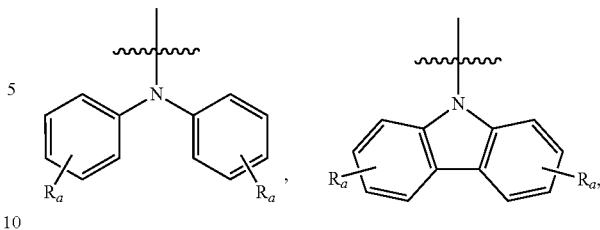

wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15) and n is 1 to 3.

Y is $R_b$,

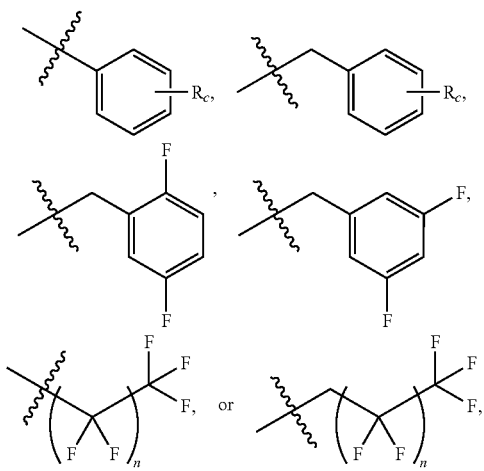

wherein $R_b$ is —H or —$C_mH_{2m+1}$ (m=1 to 15), $R_c$ is —H, —$C_mH_{2m+1}$ (m=1 to 15), —$OC_pH_{2p+1}$ (p=1 to 15) or —$SC_rH_{2r+1}$ (r=1 to 15), and n is 1 to 3.

Z is $R_a$, —$N(R_a)_2$, —COOH, —CN, —$CONH_2$, —$PO_3H_2$,

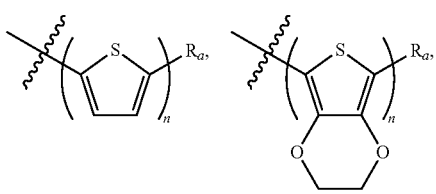

—$R_d$, or —$CONHR_d$, wherein $R_a$ is —H, —$C_mH_{2m+1}$ (m=1 to 15), —$OC_pH_{2p+1}$ (p=1 to 15) or —$SC_rH_{2r+1}$ (r=1 to 15), $R_d$ is —$C_6H_5$ or —$C_mH_{2m+1}$ (m=1 to 15), and n is 1 to 3.

Ruthenium complexes (I) and (II) above can be prepared as the followings: At first, an imidazole is reacted with 2-halopyridine to form a substituted 2-(1H-imidazol-1-yl)-pyridine. The resulting 2-(1H-imidazol-1-yl)-pyridine is alkylated with an alkylation reagent to yield, an imidazole salt having the chemical structure below. Moiety Z' is the above mentioned Z substituent or a masked form of the Z moiety above. For example, Z' can has an amine functional group when the Z substituent is unmasked, or Z' can has an ester or a nitrile functional group when the substituent is masked.

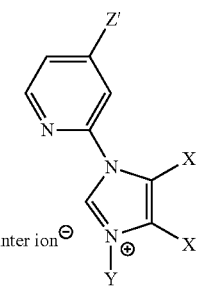

The substituted imidazole salt is then reacted with [RuCl₂(p-cymene)]₂, a ligand, and KSCN to form an protected photosensitizer. For the ruthenium complex (I), the ligand is a protected 4,4'-bis(alkoxycarbonyl)-2,2'-bipyridine. For the ruthenium complex (II), the ligand is the imidazole salt above. Finally, the masked photosensitizer was hydrolyzed under basic conditions to yield the ruthenium complex (I) or (II).

Accordingly, the following compounds were synthesized and their cell performances were evaluated to demonstrate that incorporating the NHC-pyridine ligand in the sensitizers could enhance the sensitizing capability of the photovoltaic devices.

EXAMPLES OF CHEMICAL STRUCTURE (I)

For the chemical structure (I), compounds CifPR, CI104, and CI108 were prepared for their photosensitizing properties evaluation. Their chemical structures are shown below, wherein the X of each structure is —H, the Y is 3,5-difluorobenzyl group for CifPR and 2,5-difluorobenzyl group for CI104, and CI108, and Z is —$CH_3$, —$CONH_2$, and —COOH for CifPR, CI104, and CI108, respectively.

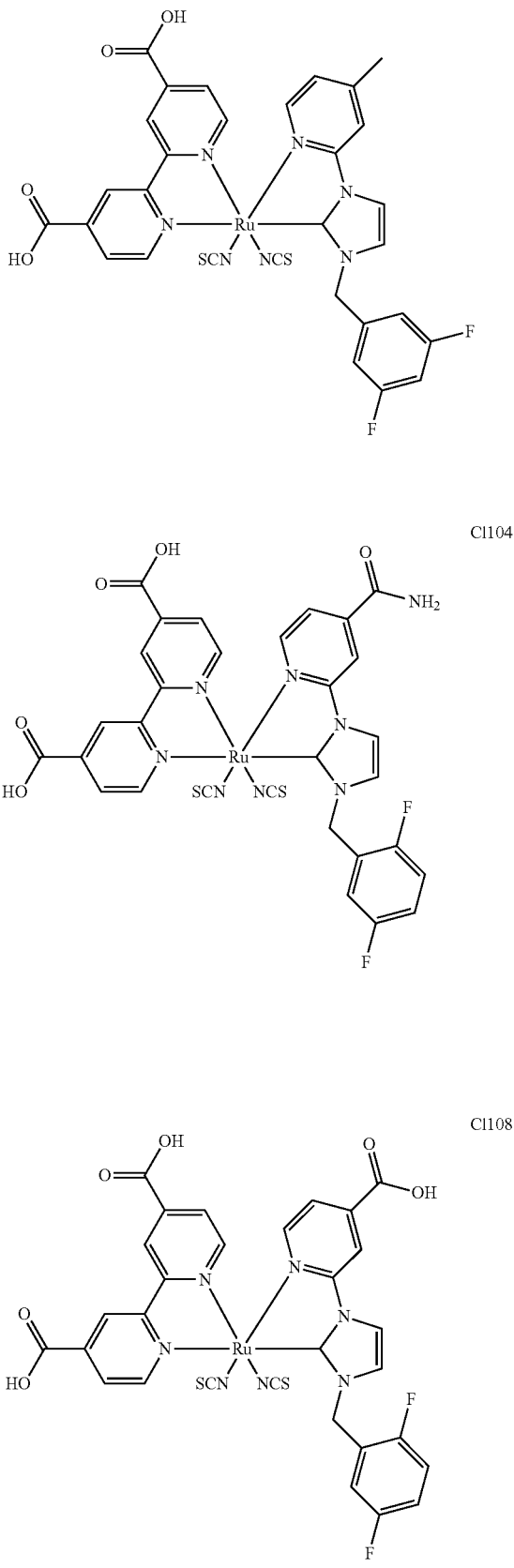

Example 1

Synthesis of CifPR

The CifPR compound was synthesized by the following chemical formulae (1) to (3).

[Chemical Formula 1]

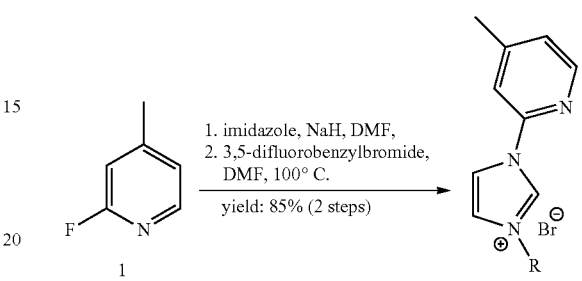

Compound 2: In a round-bottom flask, compound 1 (200 mg, 1.80 mmol) and imidazole (147 mg, 2.16 mmol) were dissolved in DMF (9 mL) at 0° C. To the above reaction mixture, sodium hydride (60% dispersion in mineral oil, 95 mg, 2.38 mmol) was added and stirred at room temperature for 10 min. The temperature of the reaction mixture was then raised to 80° C. and maintained overnight. The resulting solution was cooled to room temperature and the solvent was evaporated under reduced pressure. After adding $CH_2Cl_2$ (50 mL), the organic phase was extracted with $H_2O$ (3×25 mL). The combined organic layer was dried ($Na_2SO_4$) and concentrated. The dried residue was dissolved in DMF (8 mL) and 3,5-difluorobenzyl bromide (410 mg, 1.98 mmol) was added to the solution, which was then stirred at 100° C. for 12 h. After the removal of solvent, the crude compound 2 (560 mg, 85% yield) was washed with ether (15 mL) and used in the subsequent reaction step without further purification. $^1$H NMR (300 MHz, $CDCl_3$): δ 2.54 (s, 3H), 6.20 (s, 2H), 6.82 (tt, J=2.4, 8.7 Hz, 1H), 7.20-7.27 (m, 3H), 7.54 (s, 1H), 8.24-8.25 (m, 2H), 8.35 (d, J=4.8 Hz, 1H), 11.80 (s, 1H).

[Chemical Formula 2]

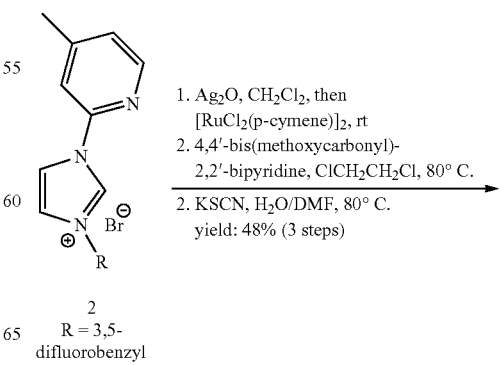

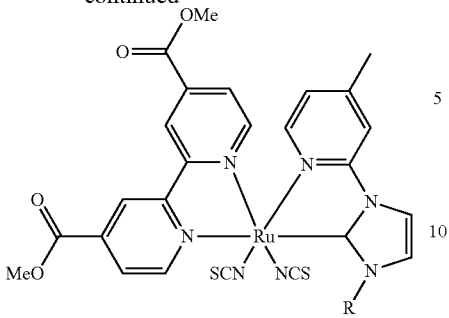

3

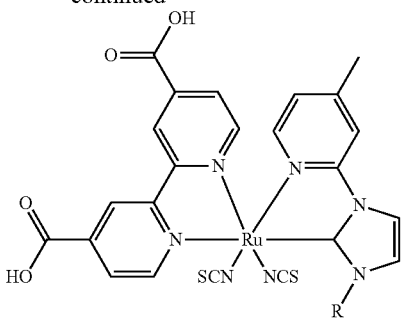

CifPR

Compound 3: To a suspension of crude compound 2 (523 mg, 1.43 mmol) in $CH_2Cl_2$ (72 mL) was added $Ag_2O$ (182 mg, 0.79 mmol) and the reaction mixture was stirred at room temperature in the dark for 6 h. After filtration of the reaction mixture through celite, $[RuCl_2(p-cymene)]_2$ (439 mg, 0.72 mmol) was added and the mixture was stirred at room temperature for another 6 h. Afterwards, the solvent was evaporated, and the resulting yellow solid was dissolved in MeOH (30 mL). After filtration through celite, the solvent was removed under vacuum. The resulting solid was dissolved with 4,4'-dimethoxy-carbonyl-2,2'-bipyridine (428 mg, 1.57 mmol) in 1,2-dichloroethane (72 mL) and the reaction mixture was stirred at 80° C. overnight. Subsequently, the solvent was removed under reduced pressure to yield a black powder. After drying, the black powder was added to the suspension of potassium thiocyanate (2.78 g, 28.60 mmol) in $H_2O/DMF$ (1:9, 43 mL). The mixture was heated at 80° C. for 12 h. After being cooled to room temperature, the solvent was removed under reduced pressure. The residue was dissolved in $CH_2Cl_2$ (150 mL), washed with $H_2O$ (3×75 mL), dried ($Na_2SO_4$) and concentrated to yield the crude product, which was purified by column chromatography (EtOAc/$CH_2Cl_2$, 1:9) and then recrystallized (ether/$CH_2Cl_2$) to afford compound 3 (534 mg, 48% yield), as deep-red crystals. $^1$H NMR (300 MHz, $d_6$-DMSO): δ 2.38 (s, 3H), 3.90 (s, 3H), 4.06 (s, 3H), 5.67 (d, J=14.7 Hz, 1H), 5.90 (d, J=14.7 Hz, 1H), 6.87 (d, J=4.8 Hz, 1H), 7.16-7.23 (m, 2H), 7.29-7.31 (m, 2H), 7.44 (dd, J=1.8, 6.0 Hz, 1H), 7.95-8.01 (m, 3H), 8.45 (dd, J=1.8, 6.0 Hz, 1H), 8.58 (d, J=2.4 Hz, 1H), 8.97 (s, 1H), 9.23 (s, 1H), 9.47 (d, J=5.7 Hz); $C_{32}H_{25}F_2N_7O_4S_2Ru$ (M) 775.0421, found 775.0427. The crystallographic data of compound 3 (CCDC 789379) can be obtained free of charge from the Cambridge Crystallographic Data Center via the linkage of www.ccdc.cam.ac.uk/data_request/cif.

[Chemical Formula 3]

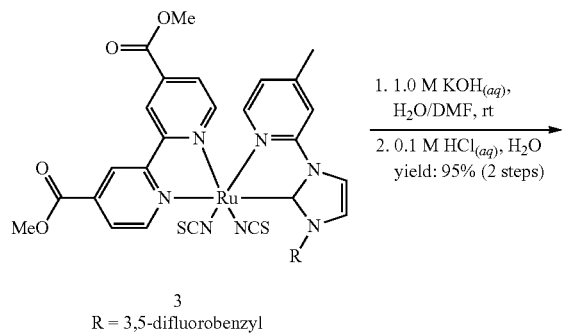

3
R = 3,5-difluorobenzyl

Sensitizer CifPR: To a solution of compound 3 (93 mg, 0.12 mmol) in $H_2O/DMF$ (1:9, 6 mL) was added 1.0 M $KOH_{(aq)}$ (0.5 mL) and the mixture was stirred at room temperature for 6 h. After the completion of hydrolysis, the solvent was evaporated under reduced pressure. The resulting residue was dissolved in water (10 mL) and the product was precipitated using 1.0 M $HCl_{(aq)}$. The resulting precipitate was filtered, washed with water (3×6 mL) and dried under vacuum to yield CifPR (85 mg, 95% yield) as a dark-red solid. $^1$H NMR (500 MHz, $d_6$-DMSO): δ 2.38 (s, 3H), 5.68 (d, J=14.5 Hz, 1H), 5.90 (d, J=14.5 Hz, 1H), 6.87 (d, J=6.0 Hz, 1H), 7.19 (t, J=9.5 Hz, 1H), 7.24 (d, J=6.0 Hz, 1H), 7.30 (s, 1H), 7.31 (s, 1H), 7.41 (dd, J=1.5, 6.0 Hz, 1H), 7.91 (d, J=6.0 Hz, 1H), 7.94 (d, J=2.5 Hz, 1H), 8.00 (s, 1H), 8.44 (d, J=5.5 Hz, 1H), 8.57 (d, J=2.5 Hz, 1H), 8.87 (s, 1H), 9.12 (s, 1H), 9.43 (d, J=5.5 Hz, 1H); $C_{30}H_{21}F_2N_7O_4S_2Ru$ is (M) 747.0108, found 747.0102.

Example 2

Synthesis of CI104

The CI104 compound was prepared by the following chemical formulae (4) to (6).

[Chemical Formula 4]

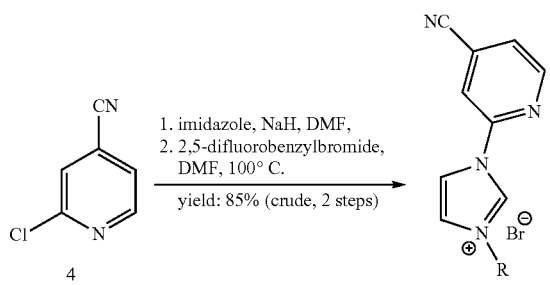

4

5
R = 2,5-difluorobenzyl

Compound 5 was prepared from compound 4 using a method similar to that described for the synthesis of compound 2. Yield: 85% $^1$H; NMR (300 MHz, $d_6$-DMSO): 5.67 (s, 2H), 7.31-7.44 (m, 2H), 7.48-7.54 (m, 1H), 8.10 (d, J=1.5 Hz, 1H), 8.15 (d d, J=0.9, 4.8 Hz, 1H), 8.60 (d, J=1.5 Hz, 1H), 8.69 (s, 1H), 8.92 (d, J=4.8 Hz, 1H), 10.33 (s, 1H).

[Chemical Formula 5]

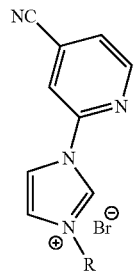

5
R = 2,5-difluorobenzyl

1. Ag₂O, CH₂Cl₂, then [RuCl₂(p-cymene)]₂, rt
2. 4,4'-bis(i-butoxycarbonyl)-2,2'-bipyridine, ClCH₂CH₂Cl, 80° C.
3. KSCN, H₂O/DMF, 80° C.
   yield: 50% (3 steps)

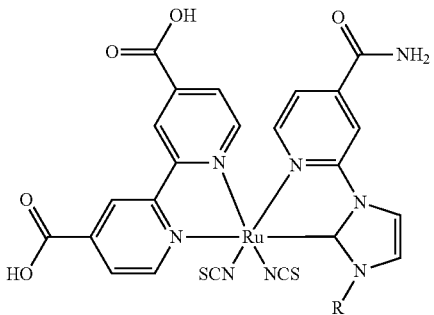

CI104

CI104 was prepared from compound 6 using a method similar to that described for the synthesis of dye CifPR. Yield: 95%; NMR (300 MHz, $d_6$-DMSO): 5.85 (d, J=15.6 Hz, 1H), 5.91 (d, J=15.6 Hz, 1H), 7.24-7.41 (m, 4H), 7.46 (dd, J=1.5, 6.0 Hz, 1H), 7.61 (d, J=6.0 Hz, 1H), 7.76 (d, J=1.8 Hz, 1H), 7.89 (s, 1H, NH), 8.04 (d, J=6.6 Hz, 1H), 8.21 (s, 1H, NH), 8.45-8.48 (m, 2H), 8.65 (d, J=2.4 Hz, 1H), 8.92 (s, 1H), 9.17 (s, 1H), 9.43 (d, J=6.0 Hz, 1H).

Example 3

Synthesis of CI108

The CI108 compound was prepared by the following chemical formulae (7) to (9).

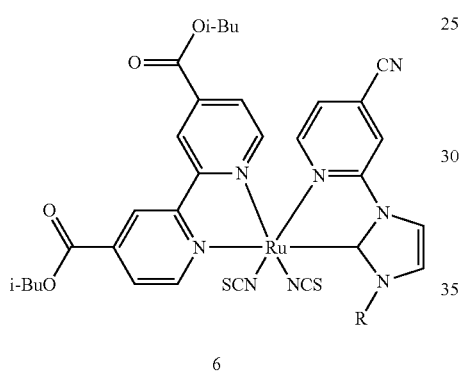

6

Compound 6 was prepared from compound 5 using a method similar to that described for the synthesis of compound 3. Yield: 50% NMR (300 MHz, $d_6$-DMSO): 0.97 (d, J=6.6 Hz, 6H), 1.08 (d, J=6.6 Hz, 6H), 1.98-2.07 (m, 1H), 2.11-2.18 (m, 1H), 4.12 (d, J=6.3 Hz, 2H), 4.27 (d, J=6.3 Hz, 2H), 5.85 (d, J=15.0 Hz, 1H), 5.93 (d, J=15.0 Hz, 1H), 7.21-7.26 (m, 2H), 7.33-7.40 (m, 2H), 7.52 (dd, J=1.5, 6.0 Hz, 1H), 7.78-7.81 (m, 2H), 8.04 (d, J=6.0 Hz, 1H), 8.55 (dd, J=1.5, 5.7 Hz, 1H), 8.65 (d, J=2.4 Hz, 1H), 8.70 (d, J=1.5 Hz, 1H), 8.93 (d, 1.5 Hz, 1H), 9.17 (s, 1H), 9.43 (d, J=5.7 Hz).

[Chemical Formula 7]

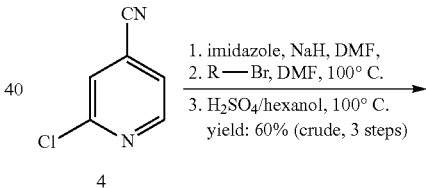

4

1. imidazole, NaH, DMF,
2. R—Br, DMF, 100° C.
3. H₂SO₄/hexanol, 100° C.
   yield: 60% (crude, 3 steps)

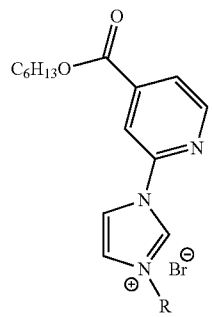

7
R = 2,5-difluorobenzyl

Compound 7 was prepared from compound 4 using a method similar to that described for the synthesis of compound 2. Yield: 60% ¹H; NMR (300 MHz, $d_6$-DMSO): 0.88 (t, J=6.9 Hz, 3H), 1.23-1.42 (m, 6H), 1.71-1.80 (m, 2H), 4.39 (t, J=6.6 Hz, 2H), 5.64 (s, 2H), 7.32-7.51 (m, 3H), 8.05-8.06 (m, 2H), 8.45 (s, 1H), 8.69 (s, 1H), 8.86 (d, J=5.1 Hz, 1H), 10.36 (s, 1H).

[Chemical Formula 6]

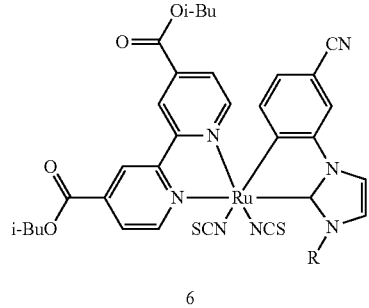

6

1. 1.0M KOH$_{(aq)}$, H₂O/DMF, rt
2. 0.1M HCl$_{(aq)}$, H₂O yield: 95% (2 steps) R = 2,5-difluorobenzyl

[Chemical Formula 8]

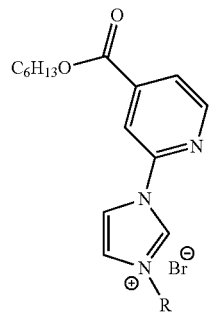

7
R = 2,5-difluorobenzyl

1. Ag$_2$O, CH$_2$Cl$_2$, then [RuCl$_2$(p-cymene)]$_2$, rt
2. 4,4'-bis(methoxycarbonyl)-2,2'-bipyridine, ClCH$_2$CH$_2$Cl, 80° C.
2. KSCN, H$_2$O/DMF, 80° C.
yield: 45% (3 steps)

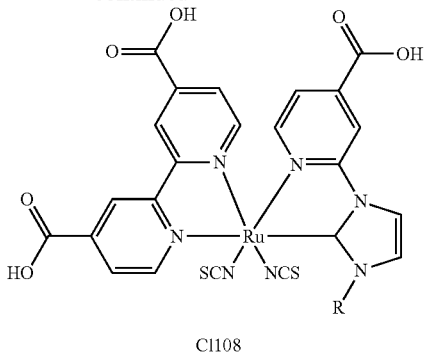

CI108

CI108 was prepared from compound 8 using a method similar to that described for the synthesis of dye CifPR. Yield: 95%; NMR (300 MHz, d$_6$-DMSO): 5.85 (d, J=15.0 Hz, 1H), 5.92 (d, J=15.0 Hz, 1H), 7.24-7.28 (m, 2H), 7.33-7.39 (m, 2H), 7.47 (dd, J=1.5, 6.0 Hz, 1H), 7.68 (d, J=6.0 Hz, 1H), 7.76 (d, J=1.8 Hz, 1H), 8.02 (d, J=6.0 Hz, 1H), 8.48 (d, J=5.4 Hz, 1H), 8.52 (s, 1H), 8.89 (d, 2.4 Hz, 1H), 8.93 (s, 1H), 9.18 (s, 1H), 9.42 (d, J=5.7 Hz, 1H).

EXAMPLES OF CHEMICAL STRUCTURE (II)

For the chemical structure (II), the compound DC102 was synthesized using a method described for the compounds in the chemical structure (I). The chemical structure of DC102 sensitizer is shown below, wherein the X of structure is —H, the Y is octyl group, and Z is —COOH.

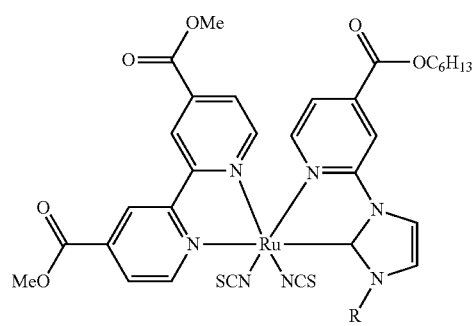

8

Compound 8 was prepared from compound 7 using a method similar to that described for the synthesis of compound 3. Yield: 45% NMR (300 MHz, d$_6$-DMSO): 0.83 (t, J=6.9 Hz, 3H), 1.24-1.36 (m, 6H), 1.61-1.70 (m, 2H), 3.91 (s, 3H), 4.07 (s, 3H), 4.28 (t, J=6.3 Hz, 2H), 5.87 (d, J=15.3 Hz, 1H), 5.93 (d, J=15.3 Hz, 1H), 7.21-7.29 (m, 2H), 7.33-7.41 (m, 2H), 7.50 (dd, J=1.5, 5.7 Hz, 1H), 7.69 (d, J=6.0 Hz, 1H), 7.77 (d, J=2.1 Hz, 1H), 8.08 (d, J=5.7 Hz, 1H), 8.51-8.54 (m, 2H), 8.92 (d, J=2.4 Hz, 1H), 9.02 (s, 1H), 9.27 (s, 1H), 9.46 (d, J=5.7 Hz, 1H).

[Chemical Formula 9]

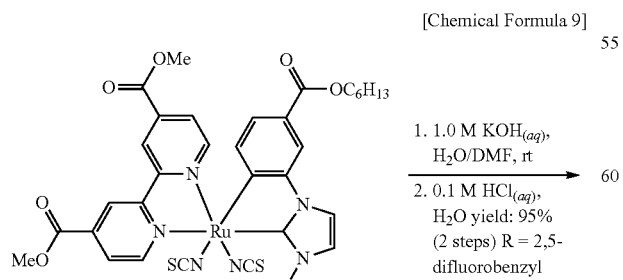

8

1. 1.0 M KOH$_{(aq)}$, H$_2$O/DMF, rt
2. 0.1 M HCl$_{(aq)}$, H$_2$O yield: 95% (2 steps) R = 2,5-difluorobenzyl

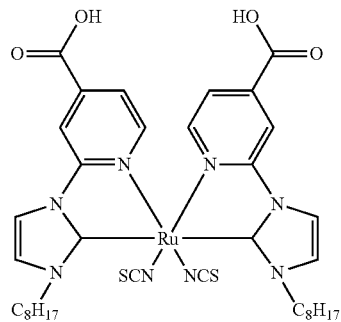

DC102

Example 5

Synthesis of DC102

The DC102 compound was prepared by the following chemical formulae (10) to (11).

[Chemical Formula 10]

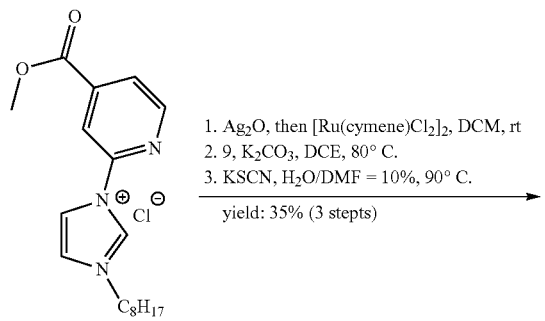

9

1. Ag₂O, then [Ru(cymene)Cl₂]₂, DCM, rt
2. 9, K₂CO₃, DCE, 80° C.
3. KSCN, H₂O/DMF = 10%, 90° C.
yield: 35% (3 stepts)

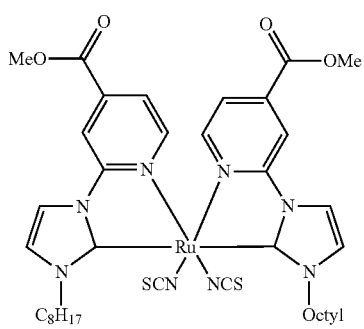

10

Compound 10 was prepared from compound 9 using a method similar to that described for the synthesis of compound 3. Yield: 35%. NMR (300 MHz, CDCl₃): δ 0.84 (t, J=6.9 Hz, 6H), 1.25-1.39 (m, 20H), 2.02-2.11 (m, 4H), 3.91 (s, 6H), 4.55-4.68 (m, 4H), 7.21 (d, J=6.0 Hz, 2H), 7.32 (d, J=2.1 Hz, 2H), 7.72 (d, J=6.0 Hz, 2H), 7.78 (d, J=2.1 Hz, 2H), 7.86 (s, 2H).

[Chemical Formula 11]

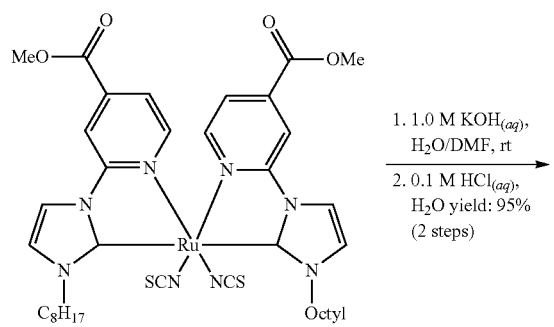

10

1. 1.0 M KOH$_{(aq)}$, H₂O/DMF, rt
2. 0.1 M HCl$_{(aq)}$, H₂O yield: 95% (2 steps)

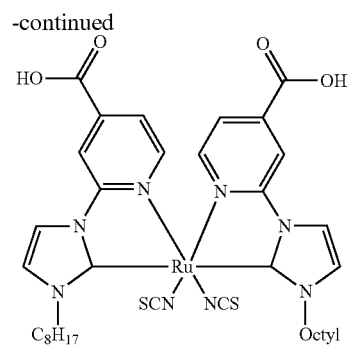

DC102

DC102 was prepared from compound 10 using a method similar to that described for the synthesis of dye CifPR. Yield: 95%. NMR (300 MHz, CD₃OD): δ 0.89 (t, J=6.9 Hz, 6H), 1.31-1.61 (m, 20H), 2.10-2.22 (m, 4H), 4.56-4.70 (m, 4H), 7.39 (d, J=6.0 Hz, 2H), 7.64 (d, J=1.8 Hz, 2H), 7.85 (d, J=6.0 Hz, 2H), 8.26 (s, 2H), 8.35 (d, J=1.8 Hz, 2H).

Fabrication and Photovoltaic Performance of Sensitized Solar Cells

To prepare a-TiO₂ (anatase-TiO₂) paste, titanium (IV) n-butoxide was mixed with 2 M CH₃COOH at room temperature and stirred until a homogeneous sol solution was obtained. The TiO₂ sol was then transferred to a Teflon-lined autoclave to perform the hydrothermal treatment at 200° C. for 5 h. The resultant solution was centrifuged with ethanol. Then the precipitate was mixed with absolute ethanol and dispersed by sonication. α-Terpineol and the mixture solution of two viscosities of ethyl cellulose (10 cps and 45 cps) in anhydrous ethanol were added into the above solution, followed by repeated sonication. Finally, the dispersed solution was concentrated. The paste was finalized after grinding by three-roller-miller grinder. The paste was coated on FTO glass and the active working area of the TiO₂ electrode was 0.16 cm². The working electrode comprised of an a-TiO₂ film and a commercial QF-1125F TiO₂ scattering layer. The electrode were then immersed in solutions containing 3×10⁻⁴ M sensitizers in 1:1 CH₃CN/tBuOH (v/v). Then Pt electrodes were placed over dye-adsorbed TiO₂ electrodes. To complete the DSSC fabrication, the electrolyte was injected into the intervening space between the TiO₂ and Pt electrodes through the two holes, which were then covered with a microscope slide and sealed.

DSSCs based on CifPR, CI108, CI104, CBTR, and N719 listed in Table 1 were all fabricated by the above procedures under the same conditions. The conventional photosensitizers CifPR, CBTR, and N719 are respectively disclosed by Dalton Trans., 2011, 40, 6765, Angew. Chem. Int. Ed. 2010, 49, 8161, and Chem. Commun., 2003, 1456-1457. In this study, we employed TiO₂ oil paste method which could be suitable for screen printing and massive production of DSSCs instead of TiO₂ water paste as reported in our earlier publications. Table 1 summarizes the corresponding short-circuit photocurrent densities ($J_{sc}$), open-circuit voltages ($V_{oc}$), fill factors ($FF_s$), and solar-to-electricity conversion efficiencies (n) of DSSCs sensitized with CifPR, CI108, CI104, CBTR, and N719 photosensitizers.

TABLE 1

Cell performance data of CifPR, CI108, CI104, CBTR, and N719-senistized solar cells.

| Photosensitizer | $J_{sc}$ (mAcm$^{-2}$) | $V_{oc}$ (mV) | FF | η (%) |
|---|---|---|---|---|
| CifPR | 17.23 | 700 | 0.67 | 8.08 |
| CI108 | 16.23 | 770 | 0.71 | 8.90 |
| CI104 | 18.25 | 770 | 0.67 | 9.45 |
| CBTR | 17.73 | 720 | 0.69 | 8.83 |
| N719 | 17.33 | 730 | 0.68 | 8.58 |

New ruthenium complexes with different NHC-pyridine ligands were designed and synthesized as photosensitizers for DSSCs to enhance the solar cell performance. Short-circuit photocurrent densities ($J_{sc}$) of DSSCs based on CifPR, CI108, and CI104 sensitizers are 17.23, 16.23, and 18.25 mA cm$^{-2}$, respectively. Surprisingly, open-circuit voltages ($V_{oc}$) of devices with CI108 and CI104 dyes are slightly higher than that of the device with N719. These results obtained could be due to the Fermi level of $TiO_2$ and the NHC-pyridine sensitizer have the similar arrangement to that of N719 dye when they bind to the conduction band of the $TiO_2$ electrode. Solar cells sensitized with CI104 and CI108 dyes exhibited higher efficiencies (9.45% and 8.90% respectively) than those of the standard N719 dye (8.58%) and our previously reported CBTR dye (8.83%). Introduction of —COOH and —CONH$_2$ electron withdrawing groups into the pyridine ring of the ancillary ligand in ruthenium complexes enhanced the efficiency of the DSSCs. From the data detailed above, the CI104-sensitized DSSC exhibits the highest photovoltaic device performance in the dye series studied. Further improvement in the efficiency of CI104 and CI108 sensitizers could be possible by the replacement of the remaining bipyridine framework using the second NHC-pyridine ligand as shown in the sensitizer DC102 in chemical structure (II).

The above results suggest that NHC-pyridine-based ruthenium complexes show promising in DSSC applications. It also indicates that the molecular design for tuning sensitizers to produce high efficiency DSSCs is important. Accordingly, replacing the traditional bipyridine unit of ruthenium polypyridine complexes resulted in DSSCs exhibiting excellent performances and sensitizing capabilities. These carbene-based ruthenium complexes can be obtained by simple, convergent, and short synthetic methods and inexpensive purification techniques. Furthermore, we found that the usage of $Ag_2O$ instead of LHMDS, as reported for the synthesis of CBTR, enhanced the reaction yields. Therefore, large-scale production of NHC-pyridine ruthenium photosensitizers could be achieved. Beside, these novel Ru—NHC complexes also may be applied as molecular probes to detect Hg, Cd, or other heavy metal ions.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. A photosensitizer for a dye sensitized solar cell, wherein the photosensitizer is a ruthenium (Ru) complex represented by the following general formula (I)

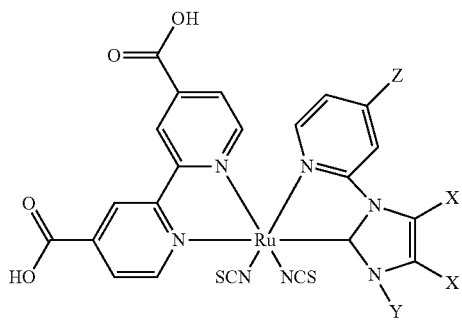

wherein X is $R_a$, $N(R_a)_2$,

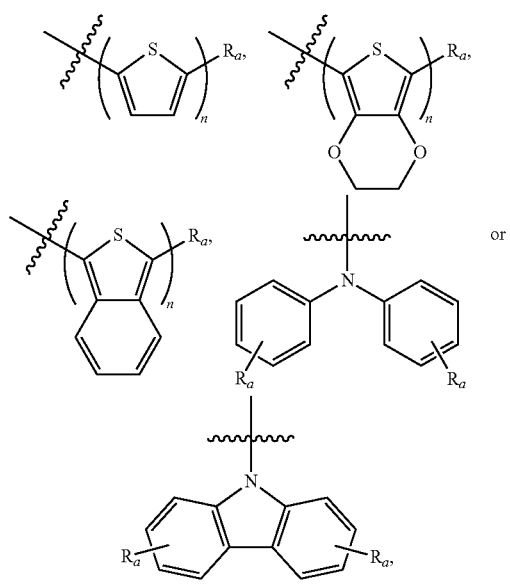

wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15) and n is 1 to 3, Y is $R_b$,

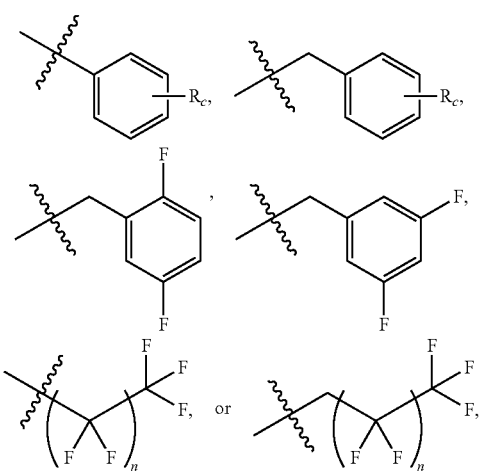

wherein $R_b$ is —H or —$C_mH_{2m+1}$ (m=1 to 15), $R_c$ is —H, —$C_mH_{2m+1}$ (m=1 to 15), —$OC_pH_{2p+1}$ (p=1 to 15) or —$SC_rH_{2r+1}$ (r=1 to 15), and n is 1 to 3, and Z is $R_a$, —$N(R_a)_2$, —COOH, —CN, —$CONH_2$, —$PO_3H_2$,

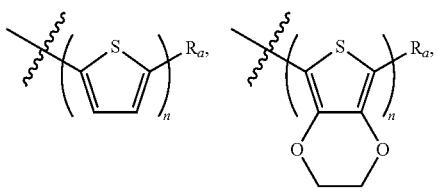

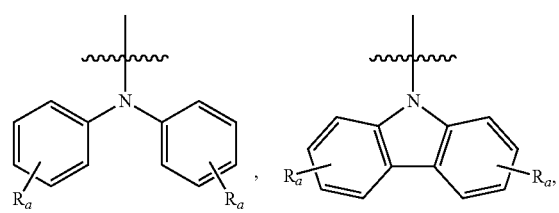

—$R_d$, or —$CONHR_d$, wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15), $R_d$ is —$C_6H_5$ or —$C_mH_{2m+1}$ (m=1 to 15), and n is 1 to 3.

2. The photosensitizer of claim 1, wherein the ruthenium complex of chemical structure (I) is CifPR, CI104, or CI108, and the chemical structures thereof are shown below.

CifPR

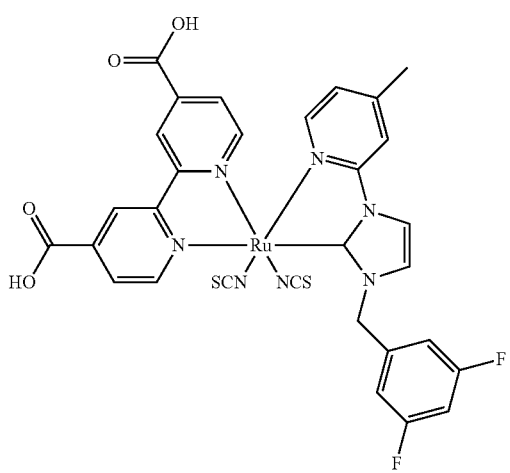

-continued

Cl104

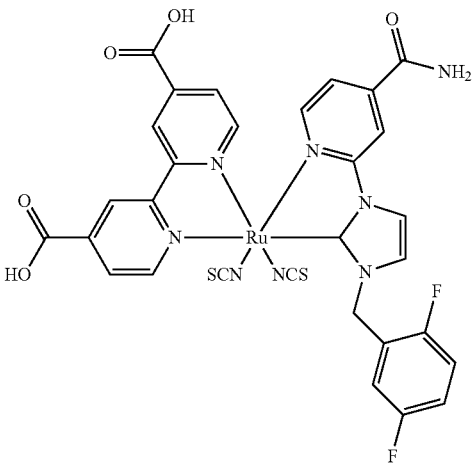

Cl108

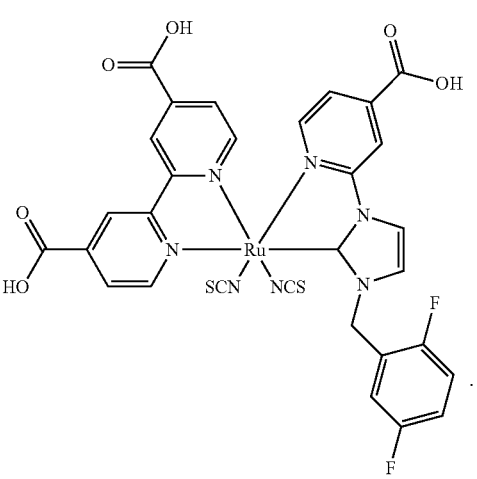

3. A photosensitizer for a dye sensitized solar cell, wherein the photosensitizer is a ruthenium (Ru) complex represented by the following general formula (II)

(II)

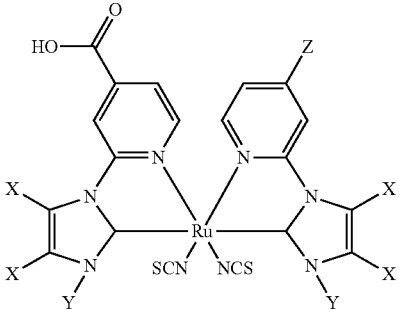

wherein X is $R_a$, $N(R_a)_2$,

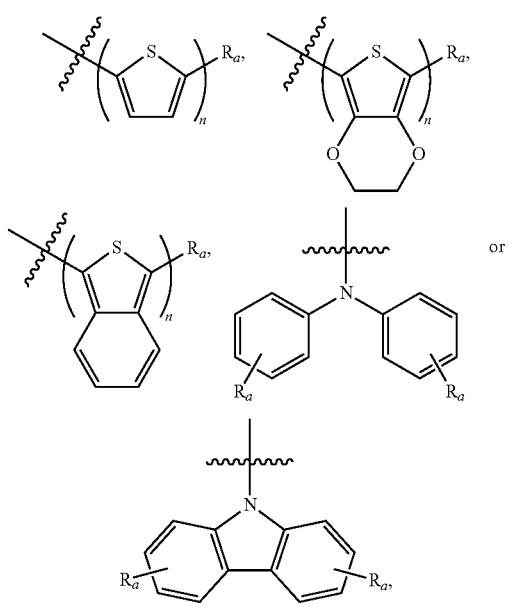

wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15) and n is 1 to 3, Y is $R_b$,

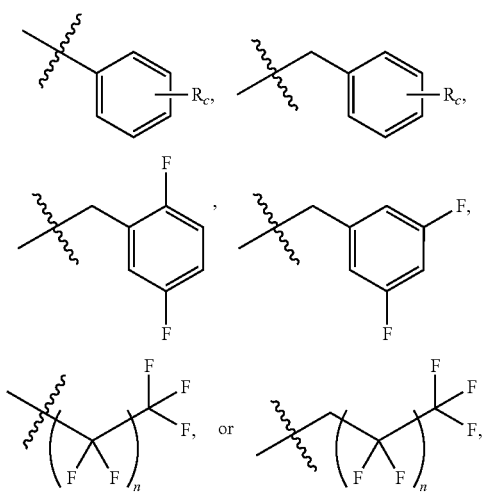

wherein $R_b$ is —H or —$C_mH_{2m+1}$ (m=1 to 15), $R_c$ is —H, —$C_mH_{2m+1}$ (m=1 to 15), —$OC_pH_{2p+1}$ (p=1 to 15) or —$SC_rH_{2r+1}$ (r=1 to 15), and n is 1 to 3, and Z is $R_a$, —$N(R_a)_2$, —COOH, —CN, —$CONH_2$, —$PO_3H_2$,

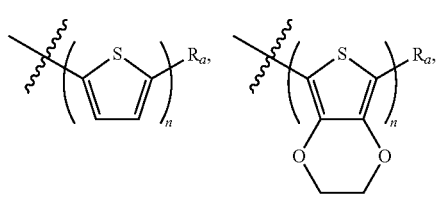

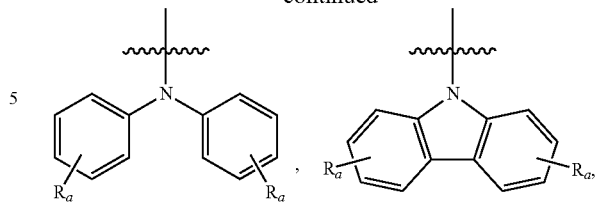

—$R_d$, or —$CONHR_d$, wherein $R_a$ is —H, —$C_6H_5$, —$C_mH_{2m+1}$ (m=1 to 15), —$OC_pH_{2p+1}$ (p=1 to 15) or —$SC_rH_{2r+1}$ (r=1 to 15), $R_d$ is —$C_6H_5$ or —$C_mH_{2m+1}$ (m=1 to 15), and n is 1 to 3.

4. The photosensitizer of claim 3, wherein the ruthenium complex of chemical structure (II) is DC102 and the chemical structure thereof is shown below.

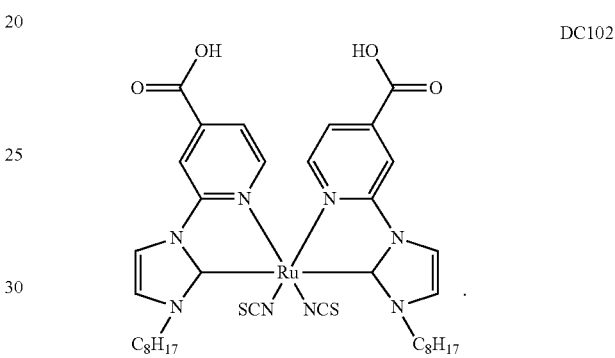

5. A method of preparing the photosensitizers of claim 1, comprising:

reacting an imidazole with a 2-halopyridine to form a substituted 2-(1H-imidazol-1-yl)-pyridine;

alkylating the substituted 2-(1H-imidazol-1-yl)-pyridine with an alkylation reagent to yield an imidazole salt, wherein the imidazole salt has the chemical structure shown below, and moiety Z' is the Z substituent in claim 1 or a masked form of the Z substituent;

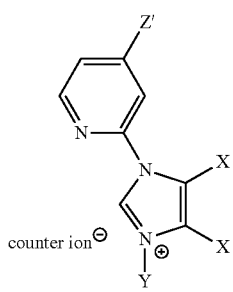

reacting the imidazole salt with [$RuCl_2$ (p-cymene)]$_2$, masked 4,4'-bis(alkoxycarbonyl)-2,2'-bipyridine, and KSCN to form the photosensitizer of claim 1 or a masked photosensitizer; and hydrolyzing the masked photosensitizer under a basic condition to yield the photosensitizer of claim 1.

6. The method of claim 5, wherein the moiety Z' has an ester functional group or a nitrile functional group when the moiety Z' is the masked form of the Z substituent.

7. A method of preparing the photosensitizers of claim 3, comprising:
- reacting an imidazole with a 2-halopyridine to form a substituted 2-(1H-imidazol-1-yl)-pyridine;
- alkylating the substituted 2-(1H-imidazol-1-yl)-pyridine with an alkylation reagent to yield an imidazole salt: wherein the imidazole salt has the chemical structure shown below, and moiety Z' is the Z substituent in claim 3 or a masked form of the Z substituent;

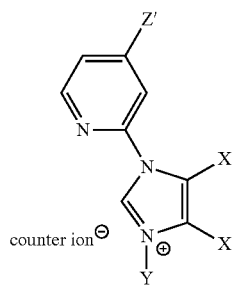

- reacting the imidazole salt with [RuCl$_2$ (p-cymene)]$_2$ and KSCN to form the photosensitizer of claim 3 or a masked photosensitizer; and
- hydrolyzing the masked photosensitizer under a basic condition to yield the photosensitizer of claim 3.

8. The method of claim 7, wherein the moiety Z' has an ester functional group or a nitrile functional group when the moiety Z' is the masked Z substituent.

* * * * *